United States Patent [19]
Katdare et al.

[11] Patent Number: 5,853,759
[45] Date of Patent: Dec. 29, 1998

[54] EFFERVESCENT ALENDRONATE FORMULATION

[75] Inventors: Ashok V. Katdare, Norristown; Kenneth A. Kramer, Green Lane; Colin R. Gardner, Blue Bell, all of Pa.

[73] Assignee: Merck & Co.. Inc., Rahway, N.J.

[21] Appl. No.: 848,460

[22] Filed: May 8, 1997

Related U.S. Application Data

[60] Provisional application No. 60/017,881, May 17, 1996.
[51] Int. Cl.⁶ .............................. A61K 9/14; A61K 9/46
[52] U.S. Cl. ............................................ 424/466; 424/489
[58] Field of Search ..................................... 424/466, 489

[56] References Cited

U.S. PATENT DOCUMENTS

| | | | |
|---|---|---|---|
| 5,270,365 | 12/1993 | Gertz et al. | 514/108 |
| 5,393,531 | 2/1995 | Gergely et al. | 424/466 |
| 5,488,041 | 1/1996 | Barbier et al. | 514/108 |
| 5,646,134 | 7/1997 | Yates | 514/108 |

FOREIGN PATENT DOCUMENTS

| | | |
|---|---|---|
| 2153225 | 8/1985 | United Kingdom . |
| 93/11774 | 6/1993 | WIPO . |
| 94/14455 | 7/1994 | WIPO . |
| 96/41618 | 12/1996 | WIPO . |

*Primary Examiner*—Thurman K. Page
*Assistant Examiner*—James M. Spear
*Attorney, Agent, or Firm*—Anthony D. Sabatelli; Joanne M. Giesser; Melvin Winokur

[57] ABSTRACT

An effervescent formulation of alendronate contains an acid source, a carbonate source, a binder, a lubricant and optionally, flavoring agents, colorants and sweeteners.

5 Claims, No Drawings

EFFERVESCENT ALENDRONATE FORMULATION

The present application claims priority to U.S. provisional application Ser. No. 60/017,881, filed May 17, 1996, now abandoned.

FIELD OF THE INVENTION

This invention relates to pharmaceutical effervescent formulations of bisphosphonates, especially alendronate, and in particular, tablets and powders which effervesce when added to water.

BACKGROUND OF THE INVENTION

There are numerous bisphosphonates which have been identifed as having utility as pharmaceutical agents which inhibit bone resorption. These include:

alendronate—(4-amino-1-hydroxy-butylidene)bis-phosphonate;
cimadronate—[(cycloheptylamino)methylene]bis-phosphonate;
clodronate—(dichloromethylene)-bis-phosphonate;
EB-1053—[1-hydroxy-3-(1-pyrrolidinyl)-propylidene] bis-phosphonate;
etidronate—(1-hydroxyethylidene)-bis-phosphonate;
ibandronate—[1-hydroxy-3-(methylpentylamino) propylidene]bis-phosphonate;
neridronate—(6-amino-1-hydroxyhexylidene)bis-phosphonate;
olpadronate—[3-(dimethylamino)-1-hydroxy-propylidene]bis-phosphonate;
pamidronate—(3-amino-1-hydroxypropylidene)bis-phosphonate;
risedronate—[1-hydroxy-2-(3-pyridinyl)-ethylidene]bis-phosphonate;
tiludronate—[[(4-chlorophenyl)thio]methylene]bis-phosphonate
YH 529—[1-hydroxy-2-imidazo-(1,2a)pyridin-3-ylethylidene]bis-phosphonate; and
zoledronate—[1-hydroxy-2-(1H-imidazol-1-yl) ethylidene]bis-phosphonate.

Alendronate has been approved by various regulatory agencies, including the Food and Drug Administration in the United States as an oral osteoporosis treatment in post menopausal women. The currently marketed formulation is a tablet, and the patient is instructed to take the tablet with a full glass of water in the morning, at least a half hour prior to eating or drinking. However, certain side effects, including esophageal irritation and erosion have been reported if the tablet was not taken with enough water, or if the patient did not remain in an upright position for approximately one-half hour after taking the medication.

It would be desirable to develop a formulation which allows a bisphosphonate to be taken orally, yet avoids problems associated with prolonged contact between the medication and the esophagus.

SUMMARY OF THE INVENTION

Not Applicable

BRIEF DESCRIPTION OF THE DRAWINGS

Not Applicable

DETAILED DESCRIPTION OF THE INVENTION

The present invention is directed to an effervescent pharmaceutical formulation comprising, as an active ingredient, a bisphosphonate seletcted from the group consisting of: alendronate, cimadronate, clodronate, EB-1053, etidronate, ibandronate, neridronate, olpadronate, pamidronate, risedronate, tiludronate, YH 529, zoledronate, pharmaceutically acceptable salts and esters of the foregoing, and mixtures of the foregoing;

an acid source selected from the group consisting of: citric acid, tartaric acid, malic acid, fumaric acid, adipic acid, succinic acid; an anhydride of said acids; an acid salt selected from the group consisting of sodium dihydrogen phosphate, disodium dihydrogen pyrophosphate and sodium acid sulfite; and mixtures of the acids, anhydrides and acid salts;

a carbonate source selected from the group consisting of: sodium bicarbonate, sodium carbonate, potassium bicarbonate, potassium carbonate, sodium sesquicarbonate, sodium glycine carbonate, and mixtures thereof;

a binder selected from the group consisting of a non-reducing sugar such as mannitol, lactose, dextrose or sorbitol; polyvinyl pyrrolidone, or, sodium chloride, sodium benzoate and sodium sulfate;

a lubricant selected from the group consisting of stearic acid salts, powdered sodium benzoate, L-leucine, sodium laurel sulfate and polyethylene glycol (PEG); and optionally, one or more additional agents selected from the group consisting of flavoring agents (such as orange and cherry) colorants, and sweeteners (including xylitol, aspartame or acesulfame K).

The present invention is also directed to an effervescent pharmaceutical formulation comprising alendronate or a pharmaceutically acceptable salt thereof as an active ingredient and an acid source selected from the group consisting of: citric acid, tartaric acid, malic acid, fumaric acid, adipic acid, succinic acid; an anhydride of said acids; an acid salt selected from the group consisting of sodium dihydrogen phosphate, disodium dihydrogen pyrophosphate and sodium acid sulfite; and mixtures of the acids, anhydrides and acid salts;

a carbonate source selected from the group consisting of: sodium bicarbonate, sodium carbonate, potassium bicarbonate, potassium carbonate, sodium sesquicarbonate, sodium glycine carbonate, and mixtures thereof;

wherein the acid source is present in at least an equivalent amount relative to the source of carbonate;

a binder selected from the group consisting of mannitol, sorbitol, polyvinyl pyrrolidone, lactose, sodium chloride sodium benzoate and sodium sulfate;

a lubricant selected from the group consisting of stearic acid salts, powdered sodium benzoate, L-leucine, sodium laurel sulfate, powdered sodium bicarbonate and polyethylene glycol (PEG); and optionally, one or more additional agents selected from the group consisting of flavoring agents, particularly orange and cherry colorants, and sweeteners selected from the group consisting of xylitol, aspartame and acesulfame K.

The effervescent pharmaceutical formulation of the present invention may be either a tablet or a powder. To use the formulation, the tablet or powders are placed in an convenient amount of water to produce an effervescent liquid, and the patient drinks the effervescent liquid.

In one embodiment the formulation is a tablet, wherein in one class the total weight of the tablet ranges from about 100 to about 50,000 mg. In another embodiment, the tablet weight ranges from about 1500 to about 32,500 mg and more particularly from about 20,800 to about 30,150 mg.

As used throughout this specification and claims, the term "bisphosphonate" is intended to include the related bisphosphonic acids and salts, and various crystalline and amorphous forms. "Alendronate" includes the related bisphosphonic acid, and salt forms. It includes crystalline, hydrated crystalline, and amorphous forms of alendronate. It specifically includes alendronate sodium and alendronate monosodium trihydrate.

Methods for the preparation of bisphosphonates are well known in the art. Methods for the preparation of alendronate and alendronate sodium salt trihydrate are known. In particular, methods for the preparation of alendronate may be found in U.S. Pat. Nos. 4,922,007, 5,019,651 and 5,510,517, each of which is hereby incorporated by reference. The amount of active in the formulation based on a weight of alendronate will range from 1 to 80 mg, particularly 5–40 mg and more particularly 5–15 mg. Exemplary amounts of alendronate are 5, 10 and 40 mg.

The formulations of this invention have many distinct advantages. First of all, the patients drinks an effervescent liquid, which limits the amount of time in which the bisphosphonate is in contact with the esophageal tissue, thus minimizing the risk of irritation. Secondly, the bioavailability of at least some of the bishosphonates, including alendronate is increased as a consequence of an excipient acting as a sequestering agent. Thirdly, the alendronate formulations are particularly advantageous in that alendronate is often prescribed to elderly patients who may experience difficulty in swallowing pills, but can more easily swallow a liquid formulation.

In preferred embodiments of the invention the acid source is chosen from acid sources which are also sequestering agents. This is an important consideration because bisphosphonates, particularly alendronate, can be a potent sequestering agent of divalent cations, especially $Ca^{2+}$ and $Mg^{2+}$. If either of these cations are present, the alendronate will sequester them, rendering the alendronate less bioavailable. Preferred acid sources which also act as a sequestering agent include citric acid and tartaric acid, and mixtures thereof. The excess citric acid or tartaric acid in the formulation binds the ions in issue and prevents their complexation with alendronate.

The carbonate source should be chosen so that it does not contain divalent cations which could be sequestered by the bisphosphonate. Suitable carbonate sources are sodium bicarbonate, sodium carbonate, potassium bicarbonate, potassium carbonate and sodium glycine carbonate. Preferred carbonate sources are sodium bicarbonate, sodium carbonate, and mixtures thereof.

In one aspect of this invention the acid source is present in an amount equal or greater than the carbonate source, on a molecular equivalent basis. Thus, when citric acid is the acid source and sodium bicarbonate is the carbonate source, the mole ratio of citric acid/bicarbonate is at least 1:3. In a particular class of this aspect there is an excess of citric acid, as this not only helps to efficiently generate the effervescence, but also acts to sequester any ions which might otherwise complex with alendronate and the excess also acts as a flavor enhancer. In an illustration of the excess acid source, the mole ratio of citric acid to bicarbonate ranges from 1:1 to 3:1. Where sodium carbonate is used as the source of carbonate an equal equivalent with citric acid will require a mole ratio of 2 moles citric acid to 3 moles carbonate. Analogous ratios can be calculated for any source of acid and carbonate, and of course the carbonate source may be present as a mixture of bicarbonate and carbonate.

For patients who exhibit gastric irritation another aspect of this invention is to employ excess amounts of the carbonate source to provide an antacid effect to the formulation. Example 2 below demonstrates such a formulation.

The binder may be a non-reducing sugar, such as mannitol, compressible lactose, dextrose or sorbitol. Alternatively, a polymer such as polyvinylpyrrolidone may be used. Other binders can include sodium chloride, sodium benzoate and sodium sulfate. The binder is usually present in approximately 3–10% of the tablet, and preferably about 5% (based on wt/wt), e.g. if the tablet weighs 1000 mg, the binder will be from about 30–100 mg, more preferably about 50 mg. If, however, a direct compression process is used to make the tablets, then a higher amount of binder is employed, preferably about 300–400 mg.

The tablet should also contain a lubricant, which typically comprises about 0.5 to about 5% of the tablet on a wt/wt basis, and preferably about 1%. Preferred lubricants include powdered sodium benzoate, micronized polyethylene glycol 6000 and polyethylene glycol 8000, sodium lauryl sulfate, powdered sodium bicarbonate and L-leucine.

For effervescent powder formulations, the composition of the powder is similar to that of the tablet, except that the lubricant is generally present in a lesser amount (about less than one-half that in the tablet) and the binder should be chosen so that it is a dry binder. In preferred formulations, the powder is granulated.

Where desired a colorant, flavoring agent such as orange or cherry or sweetner from the group xylitol, aspartame, or acesulfame K may be added to the formulation. Various methodologies for preparing the formulations of the current invention are illustrated in the examples below.

The following formulations and manufacturing procedures can be used for manufacture of effervescent tablets containing alendronate sodium.

It should be understood that one skilled in this art will recognize equivalent formulations which are intended to be included with the scope of this invention.

EXAMPLE 1

| | | |
|---|---|---|
| Alendronate sodium | 5–10 | 10 mg |
| (in mg alendronate acid) | | |
| Citric acid, anhydrous (granular) | 600–700 | 650 mg |
| Sodium bicarbonate (granular) | 300–500 | 367 mg |
| Sodium carbonate, anhydrous | 20–60 | 40 mg |
| Flavoring agent (optional) | 10–50 | 25 mg |
| Colorant (optional) | 0–10 | 5 mg |
| Sodium benzoate | 5–15 | 7.5 mg |
| Water | 0–5 | 2 mg. |

Premix sodium benzoate with sodium bicarbonate and alendronate sodium. Mix color with sodium carbonate. Place citric acid in a bowl of a suitable blender. Add the 2 mg water to the citric acid slowly and mix thoroughly to form a moist blend. Add to the blend, in sequence, while mixing, the sodium bicarbonate mix, and the sodium carbonate-color mix until uniformly distributed. Compress tablets using suitable size tooling. Cure the tablets, cool and package in aluminum foil.

EXAMPLE 2

| | | |
|---|---|---|
| Alendronate sodium (in mg alendronate acid) | 5–10 | 5 mg or 10 mg |
| Citric acid, anhydrous (granular) | 450–650 | 590 mg |
| Sodium bicarbonate (granular) | 750–1000 | 850 mg |
| Sodium bicarbonate, powder | 50–150 | 87 mg |
| Citrus flavor (optional) | 0–50 | 25 mg |
| Water | 0–25 | 15 mg. |

Blend alendronate sodium, citric acid and citrus flavor in a suitable blender. Quickly add all of water and mix until a workable mass is formed. Granulate through a suitable screen using a granulator. Spread evenly on a paper-lined tray or a fluid bed dryer. Place a dried granulation in a suitable blender and add powder sodium bicarbonate. Mix well. Compress tablets using a suitable flat face beveled edge tooling. Package in aluminum foil or aluminum tubes.

EXAMPLE 3

| | |
|---|---|
| Alendronate sodium (in mg alendronate acid) | 10 mg |
| Mannitol, direct compression grade | 165 mg |
| Sodium bicarbonate | 850 mg |
| Citric acid | 530 mg |
| Sodium benzoate | 15 mg |

Mix alendronate sodium and sodium benzoate in a suitable mixer. Add mannitol and continue mixing till uniform. Add sequentially citric acid and sodium bicarbonate. Roller compact the powder mix followed by granulation using a suitable screen. Compress the granulation using a suitable tooling. Package the tablets in aluminum foil.

EXAMPLE 4

| | | |
|---|---|---|
| Alendronate sodium (in mg alendronate acid) | 2.5–10 | 10 mg |
| Citric acid, anhydrous (granular) | 400–800 | 600 mg |
| Sodium bicarbonate (granular) | 1000–2000 | 1500 mg |
| Sodium carbonate, anhydrous | 20–80 | 40 mg |
| Flavoring agent (optional) | 0–50 | 25 mg |
| Colorant (optional) | 0–15 | 5 mg |
| Sodium benzoate | 25–175 | 150 mg |
| Xylitol | 100–300 | 200 mg |
| Sweetner (aspartame) | 1–10 | 2.5 mg |

Part 1. Blend in a suitable mixer xylitol, alendronate and 400 mg sodium bicarbonate. Roller compact this mixture.

Part 2. Blend in a suitable mixer sodium benzoate, citric acid, 900 mg sodium bicarbonate, color, flavor and sweetner; then roller compact this mixture.

Part 3. Granulate Parts 1 and 2 through a suitable screen, add remaining powders and mix.

Compress the granulation using a suitable tooling. Package the tablets in aluminum foil.

What is claimed is:

1. A formulation comprising (in mg):

| | |
|---|---|
| Alendronate sodium (in mg alendronic acid) | 5–10 mg |
| citric acid | 600–750 |
| sodium bicarbonate | 300–500 |
| sodium carbonate | 20–60 |
| sodium benzoate | 5–15 |
| water | 0–5. |

2. A formulation according to claim 1, further comprising a flavoring agent or a colorant.

3. A formulation comprising (in mg):

| | |
|---|---|
| Alendronate sodium (in mg alendronic acid) | 5–10 |
| citric acid | 450–650 |
| sodium bicarbonate (total) | 800–1150. |

4. A formulation comprising (in mg):

| | |
|---|---|
| Alendronate sodium (in mg alendronic acid) | 2.5–10 |
| citric acid | 400–800 |
| sodium bicarbonate | 1000–2000 |
| sodium carbonate | 20–80 |
| sodium benzoate | 25–175 |
| xylitol | 100–300. |

5. A formulation made by the process of combining:

| | |
|---|---|
| Alendronate sodium (in mg alendronic acid) | 2.5–10 |
| citric acid | 400–800 |
| sodium bicarbonate | 1000–2000 |
| sodium carbonate | 20–80 |
| sodium benzoate | 25–175 |
| xylitol | 100–300. |

\* \* \* \* \*